United States Patent [19]

Michaels

[11] 4,223,061

[45] Sep. 16, 1980

[54] HYDROPHILIC LAMINATE USEFUL FOR MAKING DISPENSING DEVICE

[75] Inventor: Alan S. Michaels, San Francisco

[73] Assignee: ALZA Corporation, Palo Alto, Calif.

[21] Appl. No.: 844,968

[22] Filed: Oct. 25, 1977

[51] Int. Cl.² .................................................. B32B 7/00
[52] U.S. Cl. .................................... 428/215; 128/260;
428/280; 428/284; 428/287; 428/913
[58] Field of Search .............. 128/260, 263, DIG. 12,
128/272.3, 284, 287; 428/280, 286, 287, 290,
304, 310, 913; 526/208

[56] References Cited

U.S. PATENT DOCUMENTS

| | | | |
|---|---|---|---|
| 2,546,705 | 3/1951 | Strawinski | 128/287 |
| 3,123,075 | 3/1964 | Stamberger | 128/287 |
| 3,480,016 | 11/1969 | Costanza et al. | 128/284 |
| 3,760,984 | 9/1973 | Theeuwes | 128/260 |
| 3,926,891 | 12/1975 | Gross et al. | 428/913 |
| 3,971,376 | 7/1976 | Wichterle | 128/260 |
| 3,987,790 | 10/1976 | Eckenhoff et al. | 128/260 |
| 3,992,562 | 11/1976 | Denzinger et al. | 526/208 |
| 3,995,631 | 12/1976 | Higuchi et al. | 128/260 |

Primary Examiner—James J. Bell
Attorney, Agent, or Firm—Paul Sabatine; Thomas E. Ciotti; Edward L. Mandell

[57] ABSTRACT

A self-powered device for dispensing a medicament is disclosed. The device comprises (1) a rigid housing defining an internal space, (2) a container in the housing formed of a stretched polymer and having a passageway connecting the container with the exterior of the device, (3) a medicament in the container, and (4) and expandable laminate surrounding the container positioned between the interior of the housing and the exterior of the container. The laminate comprises (a) a lamina of an absorbent material laminated to (b) a lamina of a swellable, hydrophilic polymer. In operation, when the device is in a biological fluid environment, fluid therefrom is imbibed by the laminate into the housing, causing the laminate to expand and exert pressure on the container, thereby shrinking the container to an unstretched state, which decreases its volume and concomitantly pumps medicament through the passageway at a controlled rate over time.

1 Claim, 5 Drawing Figures

HYDROPHILIC LAMINATE USEFUL FOR MAKING DISPENSING DEVICE

CROSS-REFERENCE TO RELATED APPLICATIONS

This application is copending with applicant's United States Patent Application Ser. No. 828,473 filed on Aug. 29, 1977, and United States Patent Application Ser. No. 862,363 filed on Dec. 20, 1977. This application and the copending applications are assigned to the ALZA Corporation of Palo Alto Calif.

AREA OF THE INVENTION

This invention pertains to a new and useful self-powered, unit device for dispensing drug. More particularly, the invention relates to a device that dispenses drug in response to force applied by a swelled polymer against a container made of a stretched polymer. The force causes the stretched polymer to recover to an unstretched polymer thereby decreasing the internal volume of the container and propelling drug from the device.

BACKGROUND OF THE INVENTION

In recent times, much research and development effort has been devoted to creating new and useful devices for dispensing drugs to a needy drug receptor site. Generally, these devices deliver drug by diffusion from a non-erodible polymer matrix, by release from an erodible polymer matrix, or by delivery from an osmotic device. While these prior art devices are useful for their intended purpose, serious shortcomings are associated with their use. For example, devices which contain drug dispersed or dissolved in a non-erodible matrix often do not exhibit zero order drug release kinetics since the drug is first removed only from the surface layers of the matrix and the distance the drug must diffuse to the surface from within the matrix increases with time. For this kind of device, essentially $t^{-\frac{1}{2}}$ kinetics are observed, with accompanying drug delivery declining over time. A serious shortcoming for devices made from an erodible polymer is the polymer's inability to dissolve or erode at a uniform rate over time. Correspondingly, for these devices, drug is not delivered to the receptor at a uniform rate over time. One shortcoming observed for osmotic devices is the need for the drug to be soluble in fluid imbibed into the device, since a drug that cannot act as its own osmotically effective solute will not imbibe fluid, and without imbibition, the drug is not pumped from the device. In view of the above presentation, it will be appreciated by those versed in the art that a critical need exists for a drug delivery device that is simple in construction, easy to make, and can dispense drug at a controlled rate over a prolonged period of time to an animal drug receptor site.

OBJECTS OF THE INVENTION

Accordingly, it is an immediate object of this invention to provide a novel and useful device for dispensing drug that overcomes the shortcomings known to the prior art.

Another object of the invention is to provide a drug dispensing device that is simple in construction and which device exhibits all the practical benefits of controlled and continuous administration of various drugs to animals including humans over a prolonged period of time.

Yet another object of this invention is to provide a drug delivery device, which device enables high concentrations of active drug to be dispensed therefrom, and which concentration of drug will not exhibit the tendency to be leached from the device, nor be decreased in potency when the device is administering drug to a needy receptor.

Still another object of the invention is to provide a drug delivery device that will deliver drug in solution, gel or semi-solid formulation, at a controlled rate over a prolonged period of time.

Other objects, features and advantages of this invention will become more apparent from the following description taken in conjunction with the accompanying specification, drawings and the claims.

SUMMARY OF THE INVENTION

The invention concerns a device for dispensing drug to a biological environment of use. The device comprises an expandable laminate surrounding a container made of a stretched polymer which is filled with drug and positioned in a rigid housing member. In operation, the device releases drug in response to the laminate imbibing fluid and expanding, thereby exerting pressure on the container, which then shrinks and urges drug from the device.

BRIEF DESCRIPTION OF THE DRAWINGS

In the drawings, which are not drawn to scale, but are set forth to illustrate various embodiments of the invention, the figures are as follows.

In the drawings and specification, like parts in related Figures are identified by like numbers. The terms appearing earlier in the specification and in the description of the drawings, as well as embodiments thereof, are further described elsewhere in the disclosure.

DETAILED DESCRIPTION OF THE DRAWINGS

Figure 1:
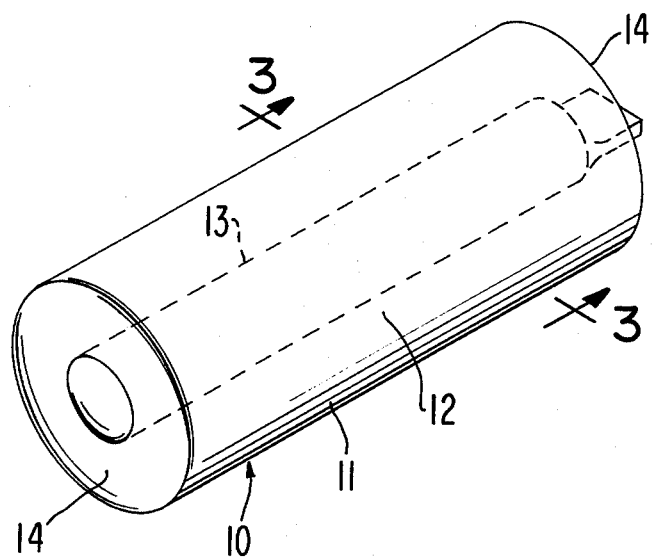
FIG. 1 is a front view, illustrating a device made with a housing member and a container placed therein.

Turning now to the drawings in detail, which are an example of a new and useful device for dispensing a drug, and which example is not to be construed as limiting, one device is illustrated in FIG. 1 by the numeral 10. In FIG. 1, device 10 consists essentially of a housing 11 shaped, sized and adapted for placement in a biological environment of use. Housing 11 is made of a substantially rigid wall-forming material, which wall surrounds and defines an internal space 12 for receiving a container 13. Housing 11 has at least one opening 14 through which container 13 communicates with the exterior of device 10. Housing 11, in another embodiment, can have a multiplicity of openings or holes 11, not shown, for admitting external fluid into housing 11. Device 10 comprises container 13 placed within housing 11 for storing a drug, which container 13 is seen in dashed lines in FIG. 1, and it is formed of a stretched polymer that relaxes to form an unstretched polymer in response to external pressure applied against the exterior surface of container 13.

Figure 2:
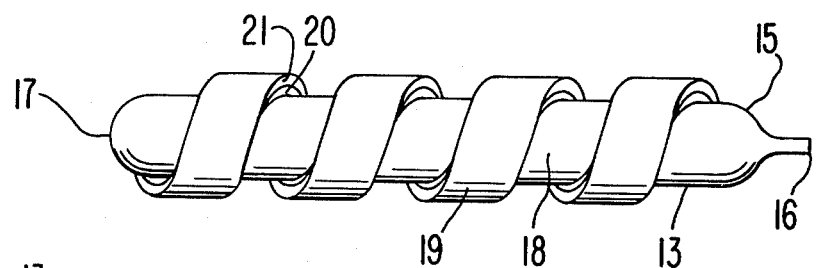
FIG. 2, taken in conjunction with FIG. 1, illustrate the device without its housing member.

FIG. 2 illustrates container 13 of device 10 of FIG. 1 free of housing 11. Container 13 has a lead end 15 that defines a passageway 16, a trailing end 17, and an exterior surface 18 surrounded in whole or in part by laminate 19. Laminate 19 is seen in FIG. 2 in spiral or helical configuration around container 13, and it consists of lamina 20 and lamina 21. Additional details pertaining to device 10 are present with the description of FIG. 3 and FIG. 4.

Figure 3:
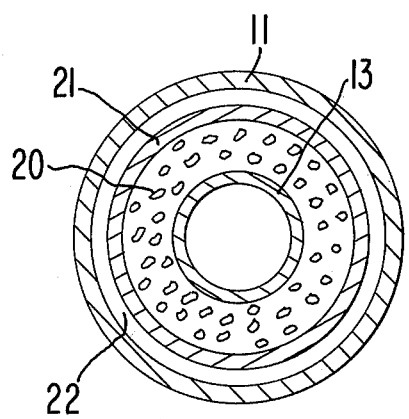
FIG. 3, is a cross-sectional view of the device of FIG. 1 through 3—3 thereof illustrating the structure of the device.

Referring to FIG. 3, dispensing device 10 is seen in cross-section along line 3—3 of FIG. 1. As seen in FIG. 3, device 10 comprises a housing 11 or body member formed of a substantially shape-retaining rigid material having positioned therein container 13. Container 13 is surrounded in whole, or in part by laminate 19, comprising lamina 20 and lamina 21. Lamina 21 is positioned adjacent to the interior surface of housing 11 distant from container 13, and it, 21, is formed of an absorbent porous or fibrous material capable of imbibing external fluid into housing 11. Fluid enters device 10 through opening 14, or in another embodiment, fluid enters through one or a multiplicity of holes in housing 11. Lamina 20 is in laminar arrangement with lamina 21, and lamina 20 is positioned adjacent to the exterior surface of container 13, distant from housing 11. Lamina 20 is formed of a swellable hydrophilic polymeric material that can imbibe fluid present in housing 11 for increasing its space-occupying 22 dimensions. In another embodiment, the laminar arrangement can consist of lamina 20 facing housing 11, with lamina 21 positioned adjacent to container 13 for producing the intended results. Container 13 is formed of a stretched polymeric material and it supports laminate 19 on its exterior surface 18.

Figure 4:
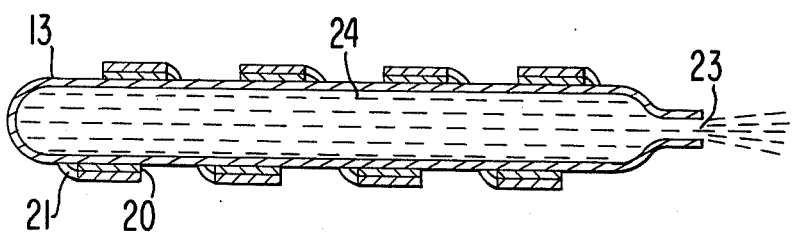
FIG. 4 is an opened-section view of the device of FIG. 2 illustrating the interior of the device; and, FIG. 5 is an illustration of the device of FIGS. 1 and 2 depicting the device in operation and dispensing drug therefrom.

FIG. 4 illustrates container 13 in opened-section, with container 13 formed with a passageway 23 for dispensing drug 24 from device 10 to a biological environment of use.

Figure 5:
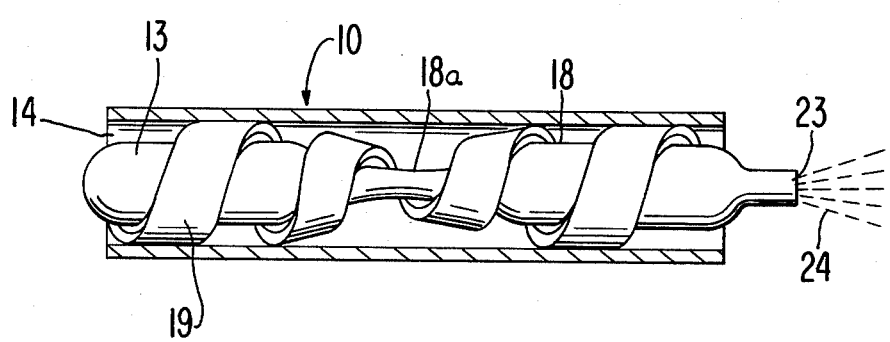

In FIG. 5, device 10 is seen dispensing drug 24 through passageway 23 from container 13. In FIG. 5, housing 11 is depicted with a part removed for illustrating container 13 and laminate 19 housed therein. In operation, device 10 functions by laminate 19 slowly imbibing water or biological fluid into laminate 19, causing laminate 20 to swell and expand, thereby exerting pressure against container 13. The pressure applied against exterior surface 18 of container 13 causes surface 18 to relax, or recover back to unstretched state 18a with an accompanying collapse in container 13. The collapse of container 13 correspondingly decrease the internal volume of container 13 thereby expelling drug 24 at a predetermined and controlled rate through passageway 23 to the environment of use over a prolonged period of time. The size of passageway 23, can in an optional embodiment, be dimensioned as an aid for controlling the rate of drug 24 released by device 10.

While FIGS. 1 through 5 are illustrative of various devices that can be made according to the invention, it is to be understood these devices are not to be construed as limiting, as they can take a wide variety of shapes, sizes and forms for delivering drug to varied and many different environments of use. For example, device 10 can be manufactured for dispensing drug 24 to animals, including warm-blooded mammals, humans, household, farm, sport and zoo animals, and for dispensing drug 24 to body cavities and body openings, such as for oral administration, intramuscular implants, intrauterine, vaginal, cervical, rectal, nasal, ear and dermal devices. Device 10 also can be made for use as an artifical gland, and for arterial and venous administration of drug 24. The device can be made for use in homes, hospitals, nursing homes and clinics.

DETAILED DESCRIPTION OF THE INVENTION

Device 10, as used for the purpose of this invention consists of a housing 11 made of a substaintally rigid polymer material. This material permits pressure to be exerted against it without any major change in its shape or dimensions, thereby assuring that pressure generated in device 10 is exerted against container 13. Housing 11 can be made from a member selected from the group consisting of a fluid impermeable polymer having at least one opening for fluid to enter device 10, and from semipermeable, permeable, or microporous materials, which materials let fluid enter device 10. Representative polymers suitable for forming housing 11 include cellulose acylates, polyolefins, polyethylene, polypropylene, polytetrafluoroethylene, polyamide, polyformaldehyde, polystyrene, polycarbonate, polyacrylate, polymethacrylate, polyacrylonitrile, polyvinyl chloride and the like. Generally, the thickness of housing 11 will vary depending on the device and its uses, and it will usually have a thickness of 1 mm to 50 mm, or more.

Representative of absorbent materials suitable for forming lamina 21 are porous materials derived from animal and plant origins including wool, cotton, straw, linen, jute, ramie, hemps, flax and other vegetable fibers. Exemplary materials include cotton mats or pads of fibers, artificial regenerated cellulose sponge, blotting paper, tea bag paper, matted, felted, porous or fibrous sheets, and other means such as absorbent bleached and unbleached paper. The thickness of lamina 21 will vary depending on the device, and it will usually have a thickness of 0.5 mm to 50 mm, or more.

Representative of swellable, hydrophilic polymers suitable for forming lamina 20 are, for example, lightly cross-linked, predominately linear polymers, such cross-links formed by covalent or ionic bonds, which polymers interact with biological fluids and swell or expand to some equilibrium state. These polymers swell to a very high degree without dissolution, usually exhibiting a 5 to 50 fold volume increase. Materials for this purpose include poly(hydroxyalkyl methacrylates), poly(acrylamide), poly(methacrylamide), poly(N-vinyl-2-pyrrolidone), anionic and cationic hydrogels, polyelectrolyte complexes, poly(vinyl alcohol) having a low acetate residual and cross-linked with glyoxal, formaldehyde or glutaraldehyde, methylcellulose cross-linked with a dialdehyde, a mixture of agar and a sodium carboxymethylcellulose, a water-insoluble, water-swellable copolymer produced by forming a dispersion of finely divided copolymer of maleic anhydride with styrene, ethylene, propylene, butylene or isobutylene cross-linked with from about 0.001 to about 0.5 mole of a polyunsaturated cross-linking agent per mole of maleic anhydride in the copolymer as disclosed in U.S. Pat. No. 3,989,586, water-swellable polymers of N-vinyl lactams as disclosed in U.S. Pat. No. 3,992,562, and the like. Generally, lamina 20 will have a thickness of about 2 mm to 50 mm and in a presently preferred embodiment, it will have an expanded or swelled thickness state approximately equal to the internal diameter of container 13 to produce a complete collapse of container 13 and discharge of drug 24 therefrom.

Representative of polymeric membranes for manufacturing container 13 are heat shrinkable polymeric films in the form of tubes and the like, which have been prepared by inducing strong molecular orientation by uni-axially or bi-axially stretching of a film, which operation, preferably can be preceded by the introduction of inter-molecular primary valence cross linkage by chemical or radiation processes. The degree of cross-linking, when used, should be sufficient to impart to the film a thermoset character, which can be conveniently defined as the ability to exhibit a minimum tensile strength of about 50 lbs/in$^2$ at a temperature of 300° F. By "heat shrinkable" is meant that the film can contract from 25 to 75 percent of its stretched dimensions, from one or more directions induced upon heating the starting material.

The polymeric film forming the wall of container 13 is expanded or stretched mechanically, hydraulically, or pneumatically, either uni-axially or bi-axially, at room temperature, or elevated temperature, and then is set or fixed, that is, frozen, into this expanded high energy state. Procedures for accomplishing this are well-known in the polymer fabrication art.

For example, in the manufacture of bi-axially oriented, heat shrinkable film, used for making a tubular container, the film is prepared by extrusion through a tube-shaping die with a circular slit of such width to give the desired tube thickness. As the hot tube of polymeric material issues from the die, it is passed over an enlarged mandrel, which tends to stretch the tube along its length and to stretch it in a circumferential direction at the same time. This operation imparts bi-axial orientation and yields a container with shrinkage along both axes. Typically, such a container will have a potential shrinkage of 50 percent in both directions.

In another manufacture of one type of heat shrinkable tubing for use in device 10 as container 13, seen in FIGS. 1 through 5, a polymer is first prepared in tubular shape by extrusion through a die having a preselected cross-sectional configuration. Then, the tubing can be subjected to ionizing radiation consisting of a stream of high energy electrons as delivered by a van de Graaff generator, or other electron accelerating equipment. Or, the tubing can be treated with gamma rays as emanating from cobalt-60. The dosage delivered can vary, depending upon the polymer, from 0.5 to 1000 megarads to achieve the desired degree of intermolecular cross-linkage. The tubing is then subjected to uniaxial molecular orientation by drawing it, optimally in a warm or heated condition, over an appropriately shaped mandrel, which can increase the cross-sectional area by a prechosen factor of 2 to 16. The polymer, having been selected from classes which tend to have high intermolecular attraction, will tend to remain in a high energy, stretched state, until placed in an environment in which these intermolecular attractions are released. This memory or tendency to recover back to the unstretched polymeric state is encouraged by the cross-linkage which was introduced by earlier radiation treatment.

In manufacture, the tube is enveloped about a mandrel and heat shrunk, briefly, for less than about a minute, exposed to elevated temperatures, advantageously in the range of 200° to 400° F., and then removed from the mandrel. Next, the laminate is wrapped around the empty tube and the resulting assembly inserted into the rigid housing. The empty container is now filled with drug formulation, and the open end of the container exposed to infra-red heat to cause shrinkage at the end. The resulting device contains an integral capillary passageway for drug discharge. The system is so selected that shrinkage of the membrane is restricted by the mandrel, such that very intimate contact is obtained, and there is sufficient reserve elastic recovery stress in the membrane to provide for assured, continuous contraction of the container in the device, as the container decreases in volume by reason of pressure on it, and by drug leaving the container.

Typical polymers that can be used for forming container 13 are the vinyl chloride polymers, including homopolymers of vinyl chloride and copolymers of vinyl chloride. The copolymers of vinyl chloride include vinyl acetate, styrene, acrylonitrile, dialkyl fumarate or maleate, and vinylidene chloride. Furthermore, blends of polyvinyl chloride, for example, with chlorinated polyethylene or ABS terpolymer, or an acrylate or methacrylate polymer can be used.

Exemplary medicaments, that is drugs, that can be administered according to the spirit of the invention include locally and systemically acting drugs. These drugs include a member selected from the group consisting of physiologically and pharmacologically acting drugs such as gastrointestinal administrable drugs, hypnotic, sedative, psychic energizer, tranquilizer, anticonvulsant, antiparkinson, muscle relaxant, analgesic, anitpyretic, anti-inflammatory, anesthetic, antispasmodic, antimicrobial, antiviral, antiulcer, hormonal, sympathomimetic, diuretic, hypoglycemic, vitamins, anti-contraceptives, and ophthalmic drug. These beneficial drugs and their dose amount for humans are known to the art in Pharmacology in Medicine, by Drill and edited by DiPalma, 1965, published by McGraw-Hill Book Company, New York; in Pharmacological Basis of Therapeutics, by Goodman and Gilman, 4th Edition, 1970, published by the MacMillian Co., London; and in U.S. Pat. No. 3,977,404, which patent is assigned to the ALZA Corporation of Palo Alto, Calif., the assignee of this patent application.

The drug in the container can be mixed with a pharmaceutically acceptable liquid carrier such as water, saline, cottonseed oil, sesame seed oil, ethyl oleate, isopropyl myristate, propylene glycol and the like. The drug can be present in solution, in semi-solid, or paste formulation, in a thixotropic state and the like, which permits controlled dispensing of drug from the device. Pharmaceutically acceptable carriers and the like are known to the art in Pharmaceutical Sciences, by Remington, 14th Edition, pages 1461 to 1762, 1970, published by the Mack Publishing Company, Easton, Pennsylvania.

Representative of a drug that can be dispensed from an oral device is as follows: (1) a rigid polyethylene housing having placed therein (2) a container shaped and sized like a 000 capsule with a single passageway and formed of stretched vinyl chloride-vinylidene chloride copolymer, which container is surrounded by (3) a monolithic laminate of polyvinyl alcohol cross-linked with glyoxal directly coated upon teabag paper without filling the pores of the paper, and a drug formulation in the container such as (4) tetracycline hydrochloride in polyethylene glycol 200, or (5) a formulation consisting of a suspension of 0.1 mg of digitoxin in a carrier medium of water, 17 weight percent, and sodium carboxyl methyl cellulose, 1.5 weight percent, which formulations in either embodiment are dispensed at a controlled rate from the device, when the device is in a fluid, environment of use.

Although the foregoing invention has been described in detail by way of illustration of a preferred embodiment and examples for purpose of clarity of understanding, it will be understood that certain changes and modifications may be practiced within the scope and spirit of the invention.

I claim:

1. A laminate useful for manufacturing a drug dispensing device wherein the laminate comprises a first lamina 0.5 mm to 50 mm thick and formed of a member selected from the group consisting of wool, cotton, felt, straw, flax and paper laminated to a second lamina 2 mm to 50 mm thick and formed of a member selected from the group consisting of poly(N-vinyl-2-pyrrolidone), methylcellulose cross-linked with a dialdehyde, a mixture of agar and sodium carboxymethylcellulose, a water-insoluble, water-swellable copolymer produced by forming a dispersion of finely divided copolymer of maleic anhydride with styrene, ethylene, propylene, butylene, or isobutylene cross-linked with from about 0.001 to about 0.5 moles of a polyunsaturated cross-linking agent per mole of maleic anhydride in the copolymer, and water-swellable polymers of N-vinyl lactams, said second lamina being selected such that in the presence of a biological fluid, a 5 to 50 fold increase in volume occurs.

* * * * *